US010987292B2

(12) United States Patent
Lewus et al.

(10) Patent No.: US 10,987,292 B2
(45) Date of Patent: Apr. 27, 2021

(54) PRESERVATIVE SYSTEM

(71) Applicant: Colgate-Palmolive Company, New York, NY (US)

(72) Inventors: Catherine Lewus, Denville, NJ (US); Laurence D. Du-Thumm, Princeton, NJ (US); Rehana Begum-Gafur, Belleville, NJ (US); Kimdra Smith-Webster, Williamstown, NJ (US); Mark Vandeven, Morristown, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/035,648

(22) PCT Filed: Nov. 11, 2013

(86) PCT No.: PCT/US2013/069514
§ 371 (c)(1),
(2) Date: May 10, 2016

(87) PCT Pub. No.: WO2015/069301
PCT Pub. Date: May 14, 2015

(65) Prior Publication Data
US 2016/0262997 A1    Sep. 15, 2016

(51) Int. Cl.
*A61K 8/368* (2006.01)
*A61Q 19/10* (2006.01)
*A61Q 15/00* (2006.01)
*A61Q 11/00* (2006.01)

(52) U.S. Cl.
CPC ............. *A61K 8/368* (2013.01); *A61Q 11/00* (2013.01); *A61Q 15/00* (2013.01); *A61Q 19/10* (2013.01); *A61K 2800/524* (2013.01); *A61K 2800/5922* (2013.01)

(58) Field of Classification Search
CPC ............ A61K 8/368; A61K 2800/5922; A61K 2800/524; A61Q 11/00; A61Q 19/10; A61Q 15/00
See application file for complete search history.

(56) References Cited

U.S. PATENT DOCUMENTS

| 2003/0165546 | A1 | 9/2003 | Resch et al. |
| 2013/0272971 | A1 | 10/2013 | Pimenta et al. |
| 2014/0005130 | A1 | 1/2014 | Kroepke et al. |

FOREIGN PATENT DOCUMENTS

| DE | 19916335 | 10/2000 |
| DE | 10156674 | 5/2003 |
| EP | 2181696 | 5/2010 |
| RU | 2118152 C1 | 8/1998 |
| WO | WO 85/003224 | 8/1985 |
| WO | WO 04/075866 | 9/2004 |

OTHER PUBLICATIONS

International Search Report and Written Opinion in International Application No. PCT/US2013/069514, dated Jul. 14, 2014.

*Primary Examiner* — Sarah Pihonak
*Assistant Examiner* — Jason Deck

(57) ABSTRACT

Provided herein is a cost-effective and potent preservative system for a composition comprising a salicylate salt and a benzoate salt in an amount of from 0.2 weight % to 0.5 weight % by total weight of the composition and in a molar ratio of salicylate to benzoate of 1:6 to 1:1.2, wherein the composition has a pH of 5 or less. Further provided herein is a method of using a combination of a salicylate salt and a benzoate salt in a preservative system in a composition, and a method of preserving a composition.

19 Claims, No Drawings

PRESERVATIVE SYSTEM

BACKGROUND

Preservative agents are incorporated into personal care compositions such as body lotions, ointments, creams and salves, to inhibit microbial growth that may, for example, arise from contamination by the consumer when in use.

Salicylate salts are effective preservative agents. However, salicylate salts are relatively expensive to use.

Therefore, it would be desirable to provide alternative preservatives that are cost-effective and effective in inhibiting microbial growth.

BRIEF SUMMARY

A composition comprising a preservative system,
wherein the preservative system comprises a salicylate salt and a benzoate salt,
wherein a total amount of the salicylate salt and the benzoate salt is from 0.2 to 0.5 weight % by total weight of the composition,
wherein a molar ratio of the salicylate to the benzoate is 1:5.55 to 1:1.11, and
wherein the pH of the composition is 5 or less.

Optionally, the preservative system consists of the salicylate salt and the benzoate salt. Further optionally, the composition is free of preservatives other than those of the preservative system.

Typically, the salicylate salt comprises sodium salicylate, and/or the benzoate salt comprises sodium benzoate.

In another aspect, provided is the use of a combination of a salicylate salt and a benzoate salt of any of the compositions defined herein as a preservative system in the composition.

In another aspect, provided is a method of preserving a composition comprising adding the preservative system defined herein to the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The term "preservation" in the context of the present invention refers to the prevention or retardation of product deterioration due to microorganisms present in the product. A "preservative agent" or "preservative" in the context of the present invention is a substance that prevents or retards the growth of microorganisms in a product.

Unless otherwise specified, all percentages and amounts expressed herein and elsewhere in the specification should be understood to refer to percentages by weight. The amounts given are based on the active weight of the material, as present in the mentioned compositions.

In one arrangement, the present invention provides a composition comprising a preservative system, wherein the preservative system comprises a salicylate salt and a benzoate salt, wherein the total amount of the salicylate salt and the benzoate salt is 0.2 weight % to about 0.5 weight % by total weight of the composition. In another arrangement, the total amount of the salicylate salt and the benzoate salt is 0.2 weight % to about 0.6 weight % by total weight of the composition.

Salicylate and Benzoate Salt

In some embodiments, the total amount of the salicylate salt and the benzoate salt is 0.25, 0.3, or 0.4 weight %, to 0.5 or 0.6 weight % by total weight of the composition. In a preferred embodiment, the total amount of the salicylate salt and the benzoate salt is 0.25 to 0.5 weight %, or 0.3 to 0.5 weight %, or 0.35 to 0.5 weight %, or 0.4 to 0.5 weight % by total weight of the composition. Optionally, the total amount of the salicylate salt and the benzoate salt is from 0.2 weight % or 0.25 weight % to 0.4 weight % by total weight of the composition. Further optionally, the total amount of the salicylate salt and the benzoate salt is 0.2 weight %, 0.25 weight %, 0.3 weight %, 0.35 weight %, 0.4 weight %, 0.45 weight %, or 0.5 weight % by total weight of the composition. Preferably, the total amount of the salicylate salt and the benzoate salt is 0.4 weight % of the total weight of the composition. It is understood that any of the mentioned concentrations may be used in combination with any of the weight ratios of salicylate salt to the benzoate salt as defined below.

In some embodiments, the molar ratio of the salicylate to the benzoate is 1:6 to 1:1.2, 1:5 to 1:1.2, 1:4.5 to 1:1.2, 1:4 to 1:1.2, 1:3.5 to 1:1.2, or 1:3 to 1:1.2, 1:2.5 to 1:1.2, 1:2 to 1:1.2, 1:5.55 to 1:1.11, 1:4.995 to 1:1.11, 1:4.44 to 1:1.11, 1:3.885 to 1:1.11, 1:3.33 to 1:1.11, 1:2.775 to 1:1.11, 1:2.22 to 1:1.11, or 1:1.665 to 1:1.11. In one embodiment, the molar ratio of the salicylate salt to the benzoate salt is 1:5.55 to 1:4.44, 1:5.55 to 1:3.33, 1:5.55 to 1:2.22, or 1:5.55 to 1:1.11. In other embodiments, the molar ratio of the salicylate salt to the benzoate salt is 1:5.217 to 1:3.33, 1:5.217 to 11:2.22, or 1:5.217 to 1:1.11. In yet other embodiments, the molar ratio of the salicylate to the benzoate may be 1:4.44 to 1:3.33, 1:4.44 to 1:2.22, or 1:3.33 to 1:2.22. The molar ratio of the salicylate to the benzoate may be 1:5.55, 1:5.217, 1:4.995, 1:4.44, 1:3.33, 1:3.885, 1:2.775, 1:2.22, 1:1.665, or 1:1.11. Reducing the proportion of salicylate is advantageous as salicylate is an expensive preservative agent. Increasing the proportion of salicylate beyond a salicylate:benzoate molar ratio of 1:1.11 is not desirable due to increased manufacturing costs.

Typically at these molar ratios, the pH of the composition is between 4 and 4.5, and preferably between 4 and 4.25. Most preferably, at these molar ratios, the pH of the composition is around 4. Typically at these molar ratios, the total concentration of the salicylate salt and the benzoate salt is greater than 0.25 or 0.3 weight % by total weight of the composition. Preferably at these molar ratios, the total concentration of the salicylate salt and the benzoate salt is 0.3 weight 0.4) to 0.4 weight % or 0.5 weight % or 0.6 weight % by total weight of the composition.

Typically, the salicylate salt is sodium salicylate and/or the benzoate salt is sodium salicylate. However, other salicylate and/or benzoate salts may be used in the preservative system. These include potassium salicylate and potassium benzoate.

In some embodiments for sodium salicylate and sodium benzoate, the weight ratio of the sodium salicylate to the sodium benzoate is 1:5 to 1:1, 1:4.5 to 1:1, 1:4 to 1:1, 1:3.5 to 1:1, 1:3 to 1:1, 1:2.5 to 1:1, 1:2 to 1:1 or 1:1.5 to 1:1. In one embodiment, the weight ratio of the sodium salicylate to the sodium benzoate is 1:5 to 1:4, or 1:5 to 1:3 or 1:5 to 1:2 or 1:5 to 1:1. In other embodiments, the weight ratio of the sodium salicylate to sodium benzoate is 1:4.7 to 1:3 or 1:4.7 to 1:2 or 1:4.7 to 1:1. In yet other embodiments, the weight ratio of the sodium salicylate to the sodium benzoate may be 1:4 to 1:3, 1:4 to 1:2, or 1:3 to 1:2. The weight ratio of the sodium salicylate to the sodium benzoate may be 1:5, 1:4.7, 1:4.5, 1:4, 1:3, 13.5, 1:2.5, 1:2, 1:1.5, or 1:1. Reducing the proportion of salicylate is advantageous as salicylate is an expensive preservative agent. Increasing the proportion of salicylate beyond a sodium salicylate:sodium benzoate weight ratio of 1:1 is not desirable due to increased manufacturing costs.

Typically at these weight ratios, the pH of the composition is between 4 and 4.5, and preferably between 4 and 4.25. Most preferably, the at these weight ratios, the pH of the composition is around 4. Typically at these weight ratios, the total concentration of the sodium salicylate and the sodium benzoate salt is greater than 0.25 or 0.3 weight % by total weight of the composition. Preferably at these weight ratios, the total concentration of the sodium salicylate and the sodium benzoate is 0.3 weight % to 0.4 weight % or 0.5 weight % or 0.6 weight % by total weight of the composition.

Preservative System

The preservative system of the present invention provides a highly effective preservative function, thereby obviating the need for any other preservative agents. In particular, salicylate and benzoate salts act in combination, in a low total concentration, to provide a highly effective system, obviating the need for further preservative agents. This enables the compositions to have reduced manufacturing costs and reduced toxicity effects that may arise from other preservative agents.

Therefore, in one embodiment, the preservative system consists of the salicylate salt and the benzoate salt. Preferably, the composition is free of preservatives other than those of the preservative system.

pH

Typically, the pH of the compositions of the present invention is 5 or less, and optionally, from 4 to 5. The inventors have found that when the pH is increased beyond 5, the preservative function of salicylate and benzoate is diminished. The pH of the compositions may be 4 to 4.5, 4.5 to 5 or 4.25 to 4.75. In some embodiments, the pH is 4, about 4.25, 4.5, 4.75 or 5. As the pH is decreased from 5, the preservative function of salicylate and benzoate is increased.

Form of Composition

Typically, the compositions of the present invention are aqueous. The carrier of the compositions may comprise demineralized water and/or softened water. Water is typically present in the compositions in an amount that is sufficient to form a liquid composition. In certain embodiments, the amount of water is at least 50 weight %, or 50 weight % to 90 weight % by total weight of the composition. In other embodiments, the amount of water is from 55 weight % to 70 weight % by total weight of the composition.

Typically, the compositions of the present invention are liquid compositions, and preferably, liquid cleansing compositions, and may take the form of a liquid, gel, lotion or foam. The compositions according to the present invention are preferably suitable for topical application to the skin and/or nails. The compositions may be applied to the skin and/or nails for therapeutic, prophylactic or cosmetic benefit. The compositions according to the present invention may for example be used for enhancing the appearance, cleansing, controlling or improving odor, and improving the feel of skin and/or nails.

The composition of the present invention may be provided, without limitation, in the forth of a body wash, shower gel or a liquid soap.

In some embodiments, the compositions may further comprise pharmaceutically or cosmetically active agents which provide a cosmetic, therapeutic or prophylactic benefit to the skin. For example, the compositions may comprise at least one cosmetically acceptable carrier selected from surfactants, humectants, emollients, thickeners, fragrances, stabilizers, colorants, antioxidants, dyes and skin care agents. Such agents and the amounts in which they may be incorporated would be known to those of ordinary skill in the art. Non-limiting examples of some such agents are provided below.

In other embodiments, the compositions of the present invention may be oral care compositions, such as dentifrice or mouthrinse compositions. In yet further embodiments, the compositions of the present invention may be antiperspirant or deodorant compositions.

Surfactants

The compositions according to the present invention may include one or more anionic surfactants, amphoteric surfactants, nonionic surfactants, cationic surfactants, and combinations thereof. Surfactants can be included in any desired amount. In one embodiment, surfactants are present in the composition in an amount of 0 to about 40% by weight. In one embodiment, the surfactants are present in an amount of about 1 to about 40% by weight. In one embodiment, surfactants are present in the composition in an amount of about 5 to about 40% by weight. In one embodiment, the surfactants are present in an amount of about 1 to about 10% by weight.

Anionic surfactants include, for example, long chain ($C_6$-$C_{22}$) alkyl materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI) long chain alkyl glyceryl ether sulfonates (AGES), sulfosuccinates and the like. Other anionic surfactants include sodium laureth sulfate, sodium pareth sulfate, and combinations thereof.

Amphoteric surfactants include, but are not limited to, derivatives of secondary and tertiary aliphatic amines in which the aliphatic radical is straight chain or branched and wherein one of the aliphatic substituents comprises about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, taurines and N-higher alkyl aspartic acids. Other equivalent amphoteric surfactants may also be used. These include high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, laurl bis-(2-hydroxyethyl)carboxy methyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like.

Examples of nonionic surfactants include, but are not limited to, polysorbate 20, long chain alkyl glucosides having $C_8$-$C_{22}$ alkyl groups, coconut fatty acid monoethanolamides such as cocamide MEA, coconut fatty acid diethanolamides, fatty alcohol ethoxylates (alkylpolyethylene glycols), alkylphenol polyethylene glycols, alkyl mercaptan polyethylene glycols; fatty amine ethoxylates (alkylaminopolyethylene glycols), fatty acid ethoxylates (acylpolyethylene glycols), polypropylene glycol ethoxylates (for example the PLURON™ block copolymers commercially available from BASF), fatty acid alkylolamides, (fatty acid amide polyethylene glycols), N-alkyl-, N-alkoxy-polyhydroxy fatty acid amides, sucrose esters, sorbitol esters, polyglycol ethers, and combinations thereof.

Examples of cationic surfactants include, but are not limited to, any quaternium or polyquaternium compound.

In another arrangement, the present invention provides a method of using a combination of a salicylate salt and a benzoate salt in a preservative system in a composition, wherein the total amount of the salicylate salt and the benzoate salt in the composition is from 0.2 to 0.5 weight % by total weight of the composition. The composition may be as defined herein.

In yet another arrangement, the present invention provides a use of a combination of a salicylate salt and a benzoate salt as a preservative system in a composition, wherein the total amount of the salicylate salt and the benzoate salt in the composition is from 0.2 to 0.5 weight % by total weight of the composition.

In a further arrangement, the present invention provides a method of preserving a composition comprising incorporating into the composition a preservative system, wherein the preservative system comprises a salicylate salt and a benzoate salt, wherein the total amount of the salicylate salt and the benzoate salt in the composition from 0.2 to 0.5 weight % by total weight of the composition. The composition may be as defined herein.

EXAMPLES

Example 1—Minimum Inhibitory Concentration Test

A minimum inhibitory concentration (MIC) test was carried out to determine the effect of the weight ratio of salicylate:benzoate and pH on the growth inhibition of *B. cepecia, P. aeruginosa, E. coli, S aureus, C. albicans* and *A. niger*.

In order to determine the minimum inhibitory concentration tier each test ratio/pH, a culture of the relevant microorganism was grown, serial dilutions of the test salicylate/benzoate composition were prepared, and a standard volume of each dilution was incubated with a standard volume of the culture. Growth of the microorganism was assessed by measuring the turbidity of the sample.

A preservative is deemed effective when growth of the microorganism is observed only when the dilution til growth (DTG) number is 6 or more. A higher DTG number indicates enhanced mirorobustness. It was observed that for the microorganisms tested, an adequate inhibition of growth was observed when the pH was less than 5. *B. cepecia* was the most resistant to the test salicylate/benzoate compositions, and therefore used as the model organism in subsequent microrobustness tests (see below). The pH effect is very strong with higher DTG at a pH of 4.5. As the pH increased, DTG decreased.

Example 2—Screening

Sodium salicylate and sodium benzoate were incorporated into a base formula typically used as a cleansing composition, in varying weight ratios, to find an effective preservative system. The base formula is illustrated in Table 1.

TABLE 1

Base formula used to screen sodium salicylate and sodium benzoate combinations

| Ingredients | % weight in Formula |
| --- | --- |
| Demineralized Water | Q.S. |
| Softened Water | 20-22 |
| Alkyl Ether Sulfate (Steol OS-270) | 10-13 |
| Polyquaternium-7 | 1-3 |
| CAP Betaine | 8-11 |
| Decyl Glucoside | 1-3 |
| Tetrasodium EDTA - 39% Soln. | 0.1-0.3 |
| Citric Acid - 50% Solution - Food Grade | 0.1-1 |

Samples of the base formula comprising sodium salicylate and sodium benzoate in different weight ratios, and in a total amount of 0.6 weight %, were subjected to a Micro Robustness Test (MRT) to assess the antimicrobial efficacy of the preservatives against *Burkholderia cepacia*. Samples of the base formula were challenged with an inoculum of bacteria. After 2, 6 and 24 hours, aliquots were tested to measure the log reduction of bacteria. Using these data, the area under the growth reduction curve (AUC) was calculated and normalized (NAUC). The AUC values represent both the rate of growth inhibition and total amount of growth inhibition. An AUC value of greater than 75 indicates acceptable preservative function.

The results are presented in Table 2.

TABLE 2

MRT test results (1)

| | | Log Reduction Summary | | | | |
| --- | --- | --- | --- | --- | --- | --- |
| # | Sample Description (weight %) | 2 Hour | 6 Hour | 24 hour | AUC | NAUC |
| 1 | Base with 0% Sodium Benzoate/100% Sodium Salicylate, pH = 4.5 | 5.72 | 5.26 | 6.72 | 135.00 | 135.68 |
| 2 | Base with 25% Sodium Benzoate/75% Sodium Salicylate, pH = 4.5 | 5.46 | 5.24 | 6.72 | 134.50 | 135.18 |
| 3 | Base with 50% Sodium Benzoate/50% Sodium Salicylate, pH = 4.5 | 4.42 | 5.10 | 6.72 | 129.84 | 130.49 |
| 4 | Base with 75% Sodium Benzoate/25% Sodium Salicylate, pH = 4.5 | 2.78 | 5.13 | 6.72 | 125.78 | 126.41 |

TABLE 2-continued

MRT test results (1)

| # | Sample Description (weight %) | 2 Hour | 6 Hour | 24 hour | AUC | NAUC |
|---|---|---|---|---|---|---|
| 5 | Base with 100% Sodium Benzoate/0% Sodium Salicylate, pH = 4.5 | 1.02 | 1.13 | 3.72 | 48.97 | 49.22 |
| 6 | Base with 0% Sodium Benzoate/0% Sodium Salicylate pH = 4.5 | 0.52 | 0.44 | 0.87 | 14.23 | 14.30 |
| 7 | Base with 0% Sodium Benzoate/100% Sodium Salicylate, pH = 5.0 | 4.08 | 5.27 | 6.72 | 130.69 | 131.35 |
| 8 | Base with 25% Sodium Benzoate/75% Sodium Salicylate, pH = 5.0 | 2.93 | 5.14 | 6.72 | 125.81 | 126.44 |
| 9 | Base with 50% Sodium Benzoate/50% Sodium Salicylate, pH = 5.0 | 2.15 | 4.06 | 6.72 | 111.59 | 112.15 |
| 10 | Base with 75% Sodium Benzoate/25% Sodium Salicylate, pH = 5.0 | 1.88 | 1.49 | 6.72 | 82.50 | 82.91 |
| 11 | Base with 100% Sodium Benzoate/0% Sodium Salicylate pH = 5.0 | 0.95 | 0.92 | 4.00 | 48.97 | 49.22 |
| 12 | Base with 0% Sodium Benzoate/0% Sodium Salicylate, pH = 5.0 | 0.44 | 0.46 | 0.52 | 11.06 | 11.12 |

It can be seen from Table 2 that when the weight ratio of salicylate to sodium benzoate is as low as 1:3 (i.e. 25 weight % salicylate, and 75 weight % benzoate), adequate microrobustness is achieved. However, when salicylate is absent (see Formula 11), adequate microbustness is not achieved.

Example 2

The preservative action of sodium salicylate and sodium benzoate in varying weight ratios and in varying total amounts was determined in a microrobustness test as described above. The results are illustrated in Table 3.

TABLE 3

MRT test results (2)

| Sample # | Sample Description (weight %) | 2 Hour | 6 Hour | 24 Hour | AUC | NAUC |
|---|---|---|---|---|---|---|
| 1 | Base w/ 50% Sodium Benzoate/50% Sodium Salicylate pH 4.5 conc. 0.4% | 2.42 | 5.48 | 5.90 | 120.64 | 137.08 |
| 2 | Base w/ 50% Sodium Benzoate/50% Sodium Salicylate pH 4.5 conc. 0.6% | 3.08 | 5.01 | 6.68 | 124.47 | 141.43 |
| 3 | Base w/ 75% Sodium Benzoate/25% Sodium Salicylate pH 4.5 conc. 0.5% | 1.68 | 3.53 | 2.68 | 67.99 | 77.25 |
| 4 | Base w/ 100% Sodium Benzoate/0% Sodium Salicylate pH 4.5 conc. 0.4% | 0.48 | 0.53 | 2.32 | 28.15 | 31.99 |
| 5 | Base w/ 100% SodiumBenzoate/0% Sodium Salicylate pH 4.5 conc. 0.6% | 0.68 | 1.42 | 5.03 | 62.93 | 71.50 |
| 6 | Base w/ 50% Sodium Benzoate/50% Sodium Salicylate pH 4.75 conc. 0.5% | 2.28 | 5.16 | 6.68 | 123.72 | 140.57 |
| 7 | Base w/ 75% Sodium Benzoate/25% Sodium Salicylate pH 4.75 conc. 0.4% | 0.80 | 1.87 | 5.64 | 73.73 | 83.77 |
| 8 | Base w/ 75% Sodium Benzoate/25% Sodium Salicylate pH 4.75 conc. 0.5% | 1.10 | 2.57 | 5.28 | 79.09 | 89.86 |
| 9 | Base w/ 75% Sodium Benzoate/25% Sodium Salicylate pH 4.75 conc. 0.5 % | 1.05 | 2.53 | 6.68 | 91.10 | 103.51 |
| 10 | Base w/ 75% Sodium Benzoate/25% Sodium Salicylate pH 4.75 conc. 0.6% | 1.28 | 3.12 | 6.68 | 98.28 | 111.67 |
| 11 | Base w/ 100% Sodium Benzoate/0% Sodium Salicylate pH 4.75 conc. 0.5% | 0.30 | 0.57 | 3.88 | 42.09 | 47.82 |
| 12 | Base w/ 50% Sodium Benzoate/50% Sodium Salicylate pH 5.0 conc. 0.4% | 0.86 | 2.08 | 6.20 | 81.26 | 92.33 |
| 13 | Base w/ 50% Sodium Benzoate/50% Sodium Salicylate pH 5.0 conc. 0.6% | 1.45 | 3.57 | 2.68 | 67.74 | 76.97 |
| 14 | Base w/ 75% Sodium Benzoate/25% Sodium Salicylate pH 5.0 conc. 0.5% | 1.06 | 1.89 | 6.68 | 84.09 | 95.55 |
| 15 | Base w/ 100% Sodium Benzoate/0% Sodium Salicylate pH 5.0 conc. 0.4% | 0.42 | 0.28 | 0.60 | 9.74 | 11.07 |
| 16 | Base w/ 100% Sodium Benzoate/0% Sodium Salicylate pH 5.0 conc. 0.6% | 0.79 | 0.57 | 0.94 | 17.10 | 19.43 |

It can be seen from Table 3 that when the salicylate: benzoate weight ratio is as low as 1:3 (i.e. 25 weight % salicylate, and 75 weight % benzoate), and the total concentration of salicylate and benzoate is as low as 0.4 weight %, adequate microrobustness is achieved. However, in the absence of salicylate see Formulae 15 and 16), adequate microrobustness is not achieved.

Example 3—pH Testing

The preservative action of sodium salicylate and sodium benzoate in varying weight ratios of up to 1:3 (i.e. 25 weight % salicylate, and 75 weight % benzoate), under varying pH conditions ranging from 4 to 4.5, and in varying total amounts, was determined in a microrobustness test as described above. The results are illustrated in Table 4. It can be seen from Table 4 that when the salicylate:benzoate weight ratio is as low as 1:5 (i.e. 17.5 weight % salicylate, and 82.5 weight % benzoate), adequate microrobustness is achieved at pH values of 4 to 4.5. However, when the weight ratio of salicylate:benzoate is reduced further (e.g. 10% salicylate:90% benzoate), adequate microrobustness is not achieved.

TABLE 4

Preservative function with varying pH, varying salicylate:benzoate ratios, and varying total concentration of salicylate and benzoate.

| # | pH | Preserv level | % salic by weight | AUC | 2 H | 6 H | 24 H |
|---|------|------|------|--------|------|------|------|
| 1 | 4.5  | 0.2  | 25   | 69.65  | 1.07 | 1.27 | 5.83 |
| 2 | 4.5  | 0.25 | 17.5 | 71.09  | 1.23 | 1.75 | 5.35 |
| 3 | 4.25 | 0.25 | 10   | 68.84  | 1.60 | 1.51 | 5.27 |
| 4 | 4    | 0.2  | 25   | 60.4   | 1.05 | 1.22 | 4.87 |
| 5 | 4.5  | 0.3  | 10   | 66.56  | 1.27 | 1.63 | 4.98 |
| 6 | 4.5  | 0.3  | 25   | 87.12  | 1.51 | 1.92 | 6.83 |
| 7 | 4.25 | 0.25 | 17.5 | 84.14  | 1.37 | 2.08 | 6.35 |
| 8 | 4.25 | 0.3  | 17.5 | 80.41  | 1.65 | 2.09 | 5.83 |
| 9 | 4    | 0.25 | 17.5 | 100.31 | 2.02 | 2.98 | 6.83 |
| 10 | 4.5  | 0.2  | 10   | 49.61  | 0.79 | 1.12 | 3.88 |
| 11 | 4.25 | 0.25 | 25   | 86.34  | 1.51 | 2.34 | 6.23 |
| 12 | 4    | 0.2  | 10   | 74.81  | 1.47 | 1.63 | 5.83 |
| 13 | 4.25 | 0.2  | 17.5 | 73.39  | 1.53 | 1.55 | 5.75 |
| 14 | 4.25 | 0.25 | 17.5 | 81.77  | 1.60 | 1.90 | 6.23 |
| 15 | 4    | 0.3  | 25   | 126.28 | 3.05 | 5.06 | 6.83 |
| 16 | 4    | 0.3  | 10   | 81.79  | 1.68 | 1.88 | 6.23 |

Example 4—pH Testing (2)

The preservative action of sodium salicylate and sodium benzoate in varying weight ratios of up to 1:1, under varying pH conditions ranging from 4 to 5, and in varying total amounts, was determined in a microrobustness test as described above. It was observed that when the salicylate: benzoate weight ratio is as low as 1:5 (i.e. about 17 weight % salicylate, and about 83 weight % benzoate) and up to 1:1 (i.e. 50 weight % salicylate, and 50 weight % benzoate), adequate microrobustness is achieved at pH values of 4 to 5 and at a total salicylate and benzoate concentration of 0.2 to 0.6 weight %. However, when the proportion of salicylate is reduced further, the microrobustness of the preservative system decreases. It may also be seen that growth inhibition using a salicylate:benzoate ratio of from 1.5 to 1:1 is more effective when the pH is from 4 to 4.5 than when the pH is from 1.5 to 5.

We claim:

1. A composition comprising a preservative system,
    wherein the preservative system comprises a salicylate salt and a benzoate salt,
    wherein a total amount of the salicylate salt and the benzoate salt is from 0.2 to 0.6 weight % by total weight of the composition,
    wherein a weight ratio of the salicylate to the benzoate is 1:5 to 1:1, and
    wherein the pH of the composition is from 4 to 4.5.

2. The composition of claim 1, wherein the molar ratio of the salicylate salt to the benzoate salt is 1:4.5 to 1:1.2.

3. The composition of claim 1, wherein the molar ratio of the salicylate salt to the benzoate salt is 1:3.4 to 1:1.2.

4. The composition of claim 1, wherein the molar ratio of the salicylate salt to the benzoate salt is 1:3.33.

5. The composition of claim 1, wherein the salicylate salt comprises sodium salicylate.

6. The composition of claim 1, wherein the benzoate salt comprises sodium benzoate.

7. The composition of claim 1, wherein the preservative system consists of the salicylate salt and the benzoate salt.

8. The composition of claim 1, wherein the composition is free of preservatives other than those of the preservative system.

9. The composition of claim 1, wherein the total amount of the salicylate salt and the benzoate salt is 0.25 to 0.4 weight %, by total weight of the composition.

10. The composition of claim 1, wherein the total amount of the salicylate salt and the benzoate salt is 0.2 weight %, 0.25 weight %, 0.3 weight %, 0.35 weight %, 0.4 weight %, by total weight of the composition.

11. The composition of claim 1, wherein the total amount of the salicylate salt and the benzoate salt is 0.4 weight % by total weight of the composition.

12. The composition of claim 1, wherein the salicylate salt is sodium salicylate and the benzoate salt is sodium benzoate.

13. The composition of claim 12, wherein the weight ratio of sodium salicylate to sodium benzoate is 1:4.7 to 1:3.

14. The composition of claim 12, wherein the weight ratio of sodium salicylate to sodium benzoate is one of 1:5, 1:4.7, 1:4.5, 1:4, 1:3, 1:3.5, 1:2.5, 1:2, or 1:1.5.

15. The composition of claim 1, wherein the composition is a liquid cleaning composition.

16. The composition of claim 12, wherein the weight ratio of sodium salicylate to sodium benzoate is 1:3, and adequate microrobustness is achieved with an AUC value of greater than 75, as compared to an inadequate microrobustness with an AUC value of lower than 75 when salicylate is absent.

17. The composition of claim 1, wherein the salicylate: benzoate weight ratio is 1:3, the total concentration of salicylate and benzoate is 0.4 weight %, and adequate microrobustness is achieved with an AUC value of greater than 75, as compared to an inadequate microrobustness with an AUC value of lower than 75 when salicylate is absent.

18. The composition of claim 1, wherein the salicylate: benzoate weight ratio is 1:5, adequate microrobustness is achieved at pH values of 4 to 4.5 with an AUC value of greater than 75, as compared to an inadequate microrobustness with an AUC value of lower than 75 when the weight ratio of salicylate:benzoate is reduced further.

19. The composition of claim 1, which is selected from body lotions, ointments, creams and salves.

* * * * *